(12) United States Patent
Deac

(10) Patent No.: US 10,271,899 B2
(45) Date of Patent: Apr. 30, 2019

(54) MULTI-FUNCTION DEVICE WITH TREATMENT AND SENSING CAPABILITIES

(71) Applicant: Medtronic CryoCath LP, Toronto (CA)

(72) Inventor: Ioana Deac, Vaudreuil-Dorion (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 904 days.

(21) Appl. No.: 14/661,713

(22) Filed: Mar. 18, 2015

(65) Prior Publication Data

US 2016/0270844 A1    Sep. 22, 2016

(51) Int. Cl.
| | |
|---|---|
| *A61B 18/14* | (2006.01) |
| *A61B 5/042* | (2006.01) |
| *A61B 5/0408* | (2006.01) |
| *A61B 18/00* | (2006.01) |

(52) U.S. Cl.
CPC ........ *A61B 18/1492* (2013.01); *A61B 5/0422* (2013.01); *A61B 5/04085* (2013.01); *A61B 2018/00357* (2013.01); *A61B 2018/00577* (2013.01); *A61B 2018/00839* (2013.01)

(58) Field of Classification Search
CPC ............ A61B 18/1492; A61B 5/04085; A61B 5/0422; A61B 2018/00357; A61B 2018/00577; A61B 2018/00839
See application file for complete search history.

(56) References Cited

U.S. PATENT DOCUMENTS

| | | | |
|---|---|---|---|
| 5,555,883 A | 9/1996 | Avitall | |
| 5,687,723 A | 11/1997 | Avitall | |
| 5,842,984 A | 12/1998 | Aviatall | |
| 5,879,295 A | 3/1999 | Li et al. | |
| 5,971,983 A | 10/1999 | Lesh | |
| 6,325,797 B1 | 12/2001 | Stewart et al. | |
| 6,607,520 B2 | 8/2003 | Keane | |
| 6,960,206 B2 | 11/2005 | Keane | |
| 6,979,331 B2 | 12/2005 | Hintringer et al. | |
| 7,590,454 B2 * | 9/2009 | Garabedian | A61N 1/0551 607/117 |
| 7,850,685 B2 | 12/2010 | Kunis et al. | |
| 8,012,127 B2 | 9/2011 | Lieberman et al. | |
| 8,206,384 B2 | 6/2012 | Falwell et al. | |
| 8,337,492 B2 | 12/2012 | Kunis et al. | |

(Continued)

*Primary Examiner* — Mark Bockelman
(74) *Attorney, Agent, or Firm* — Christopher & Weisberg, P.A.

(57) ABSTRACT

A device, method, and system for adding mapping functionality to an ablation device without adding electrodes, wiring, or other components to the ablation device. The device includes a treatment catheter including a proximal portion and a distal portion, the distal portion including a longitudinal groove. The device also includes a mapping catheter including a proximal portion and a distal portion, the distal portion of the mapping catheter being coupled to the distal portion of the treatment catheter. For example, the distal portion of the mapping catheter is snapped into the groove of the treatment catheter. Together the treatment and mapping catheters are transitionable between a variety of configurations. In this way, the medical device may be used to both treat and map tissue without complicating the design and manufacture of the treatment catheter.

10 Claims, 8 Drawing Sheets

(56) References Cited

U.S. PATENT DOCUMENTS

| | | |
|---|---|---|
| 8,419,731 B2 * | 4/2013 | Pellegrino .......... A61B 17/3472 606/41 |
| 8,679,105 B2 | 3/2014 | Wittenberger et al. |
| 8,682,410 B2 | 3/2014 | Werneth et al. |
| 8,771,267 B2 | 7/2014 | Kunis et al. |
| 8,929,969 B2 | 1/2015 | Gillis et al. |
| 8,961,509 B2 | 2/2015 | Falwell et al. |
| 8,979,841 B2 | 3/2015 | Kunis et al. |
| 2006/0135953 A1 | 6/2006 | Kania et al. |
| 2008/0009851 A1 | 1/2008 | Wittenberger et al. |
| 2008/0281312 A1 | 11/2008 | Werneth et al. |
| 2009/0005769 A1 | 1/2009 | Haywood |
| 2010/0114269 A1 | 5/2010 | Wittenberger et al. |
| 2011/0054464 A1 | 3/2011 | Werneth et al. |
| 2012/0035601 A1 | 2/2012 | Wittenberger |
| 2012/0232374 A1 | 9/2012 | Werneth et al. |
| 2012/0245577 A1 | 9/2012 | Mihalik et al. |
| 2012/0283722 A1 | 11/2012 | Asconeguy |
| 2013/0006238 A1 | 1/2013 | Ditter et al. |
| 2013/0030425 A1 | 1/2013 | Stewart et al. |
| 2014/0163347 A1 | 6/2014 | Werneth et al. |
| 2014/0276712 A1 | 9/2014 | Mallin et al. |
| 2014/0276727 A1 | 9/2014 | Guala |

\* cited by examiner

MULTI-FUNCTION DEVICE WITH TREATMENT AND SENSING CAPABILITIES

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a device, method, and system for adding mapping functionality to an ablation device without adding electrodes, wiring, or other components to the ablation device.

BACKGROUND OF THE INVENTION

Percutaneous catheter ablation is a well-established technique for treating cardiac arrhythmia by targeting tissue at the site of the abnormal electrical activity. Various forms of ablative energy may be delivered via a transvenous catheter. The most common transvenous catheters are radiofrequency (RF) ablation and cryotherapy. Atrial fibrillation (AF), the most frequently occurring supraventricular tachyarrhythmia, may be initiated by ectopic heart beats that originate in or around the ostia of the pulmonary veins. The isolation of pulmonary veins (referred to as pulmonary vein isolation, or PVI) has been demonstrated to be the cornerstone of paroxysmal AF treatment.

Literature suggests that other structures or sites may participate in triggering or sustaining AF. Electrogram-guided ablation of complex atrial fractionated electrograms (CAFEs), ganglionated plexi (GPs), and other sites and structures (substrate modification) can be considered as target sites for targeting treatment for terminating AF.

A number of devices have been proposed that provide ablation and mapping capabilities so that a single device may be used to not only detect sites that support AF, but also may be used to treat such sites and terminate AF using electrogram-guided ablation. However, these devices have several drawbacks. First, a versatile catheter is desired that can provide not only wide-area ablation, but that can also create focal and/or circular lesions. However, these devices do not provide electrogram (EGM) sensing capabilities on the ablation element. Therefore, the treatment area of the device must be manipulated within the patient between a mapping configuration and an ablation configuration, which complicates the treatment procedure. Second, combining functionalities such as mapping and cryoablation into a multi-function catheter may increase the likelihood that leaks develop and gas egress into the heart occurs. Third, the integration of multiple functionalities into a single device significantly increases the cost and complexity of its fabrication and can result in a device that is larger than is optimal in order to accommodate the device components within. This increase in size can make navigation of the device within the patient difficult and is also more likely to injure the patient.

It is therefore desirable to provide a multi-function catheter that is capable of both mapping and treating tissue. It is further desirable to provide a multi-functionality device that is capable of creating a variety of ablation patterns, such as wide-area, focal, and circular ablation patterns, and that does not necessitate the inclusion of an increased amount of device and/or system components over those required for an ablation device alone.

SUMMARY OF THE INVENTION

The present invention advantageously provides a device, method, and system for adding mapping functionality to an ablation device without adding electrodes, wiring, or other components to the ablation device. The device may include a first elongate body including a first proximal portion and a first distal portion, the first distal portion including a longitudinal groove and a second elongate body including a second proximal portion and a second distal portion, the second distal portion being coupled to the first distal portion. For example, the second distal portion may be received and retained within the groove in the first distal portion. Further, in contrast to the first and second distal portions, the first proximal portion and the second proximal portion may be uncoupled to each other (for example, in a side-by-side relationship). The first elongate body may include a plurality of thermally transmissive regions, such as electrodes. For example, the first elongate body may define a distal tip and an outer lateral surface, and the plurality of electrodes may include a distal tip electrode and a plurality of electrodes on the outer lateral surface of the first elongate body. The plurality of electrodes on the outer lateral surface of the first elongate body may not traverse the longitudinal groove. The plurality of electrodes may in electrical communication with a radiofrequency energy source, and/or the plurality of thermally transmissive regions may be in thermal communication with a source of refrigerant. The second elongate body may include a plurality of mapping electrodes. When the coupled together, the first distal portion and the second distal portion may be transitionable between an at least substantially linear first configuration and an at least substantially circular second configuration. Further, the first elongate body may include a plurality of treatment electrodes and the second elongate body may include a plurality of mapping electrodes, and treatment energy may be delivered from the plurality of treatment electrodes and mapping data may be recorded by the plurality of mapping electrodes when the distal portion of the first elongate body and the distal portion of the second elongate body are coupled together.

A medical system for treating and mapping tissue may include a first elongate body including a first proximal portion and a first distal portion, the first distal portion including a longitudinal groove and a plurality of thermally transmissive regions; a second elongate body including a second proximal portion and a second distal portion, the second distal portion including a plurality of mapping electrodes and being coupled to the first distal portion; and a control unit in communication with the first elongate body and the second elongate bodies. Further, the coupled first distal portion and the second distal portion together may be transitionable between an at least substantially linear first configuration and an at least substantially circular second configuration. The first distal portion and the second distal portion may be coupled to each other when the first elongate body and the second elongate body are within a patient's body and the first proximal portion and the second proximal portion may be uncoupled from each other when the first elongate body and the second elongate body are within the patient's body. The plurality of thermally transmissive regions may be electrodes and the control unit may include a radio frequency energy source that is in electrical communication with the plurality of electrodes. Additionally or alternatively, the first elongate body may define a fluid delivery lumen and the control unit may include a refrigerant source, the fluid delivery lumen being in fluid communication with the refrigerant source and in thermal communication with the plurality of thermally transmissive regions.

A method of mapping and treating cardiac tissue may include positioning at least a portion of a medical device within a patient's heart, the medical device including: an ablation catheter having a proximal portion and a distal portion having a plurality of treatment electrodes and defining a longitudinal groove; and a mapping catheter having a proximal portion and a distal portion having a plurality of mapping electrodes, the distal portion of the mapping catheter being within and retained by the longitudinal groove of the ablation catheter; positioning the medical device such that the plurality of mapping electrodes are in contact with an area of tissue of the patient's heart; recording mapping data while the mapping catheter is within and retained by the longitudinal groove of the ablation catheter; positioning the medical device such that the plurality of treatment electrodes are in contact with an area of tissue of the patient's heart; and delivering ablation energy from the plurality of treatment electrodes while the mapping catheter is within and retained by the longitudinal groove of the ablation catheter. The distal portion of the treatment catheter and the distal portion of the mapping catheter may together define a distal portion of the medical device when the distal portion of the mapping catheter is within and retained by the longitudinal groove of the ablation catheter, and the distal portion of the medical device may be transitionable between an at least substantially linear first configuration and an at least substantially circular second configuration. Unlike the distal portions, the proximal portion of the treatment catheter and the proximal portion of the mapping catheter may not be coupled to each other when the at least a portion of the medical device is within the patient's body.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
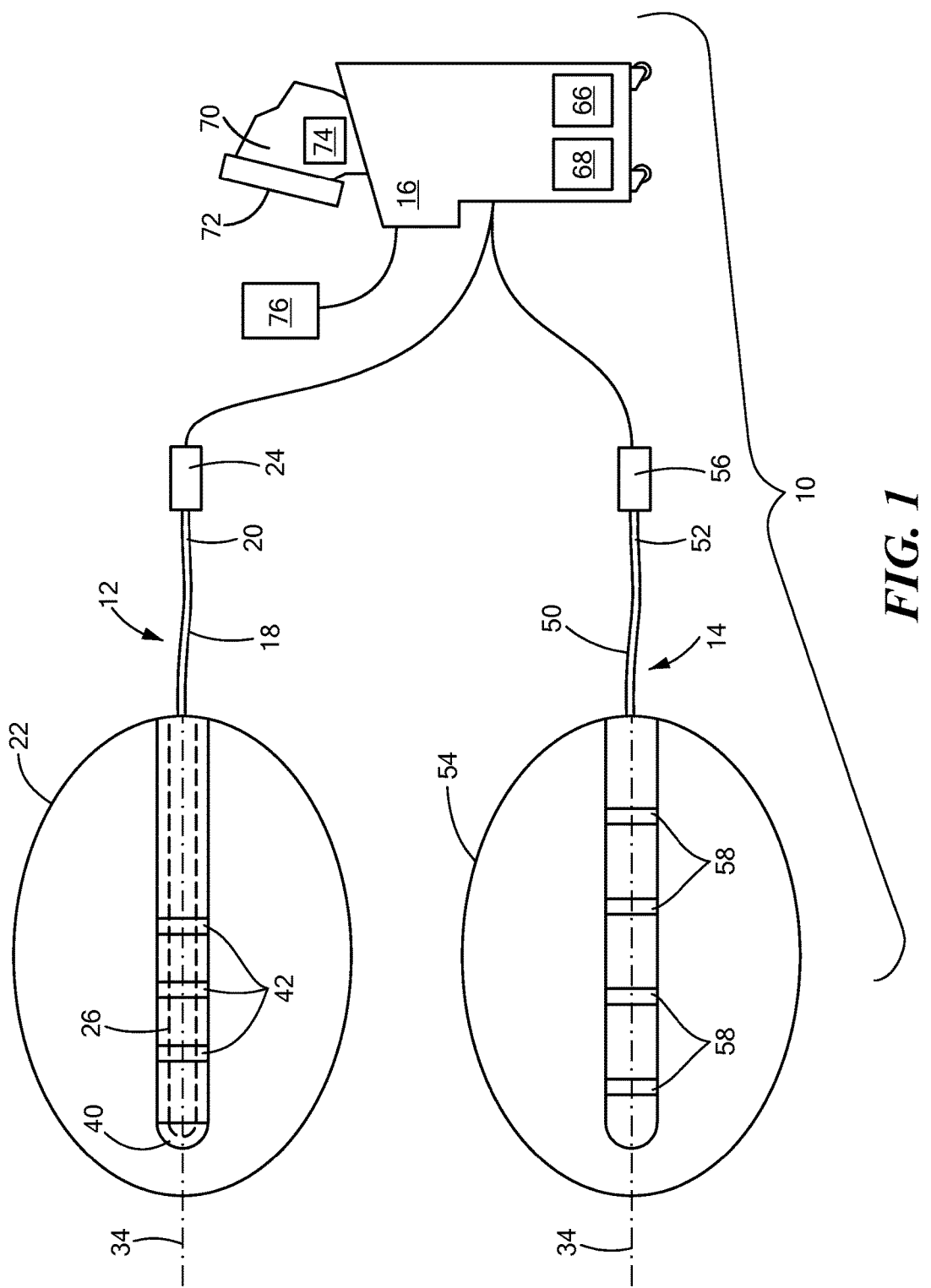
FIG. 1 shows an exemplary system that includes a treatment device and a mapping device that are coupled together to create a multi-function medical device.

Referring now to the figures in which like reference numbers designate like elements, FIG. 1 shows an exemplary system that includes a treatment device and a mapping device that are coupled together to create a multi-function medical device. The system 10 may generally include a treatment device 12, a mapping device 14, and a control unit 16. As used herein, the term "control unit" may include any system component that is not part of the treatment device 12 or the mapping device 14, whether or not physically located within the control unit 16.

The treatment device 12 may include an elongate body 18 having a proximal portion 20 and a distal portion 22. The proximal portion 20 of the elongate body 18 may be coupled to and in mechanical communication with a handle 24 having one or more steering actuators (not shown). Depending on the energy modality used, the treatment device 12 may also include one or more lumens, such as a fluid injection lumen 26 and/or one or more lumens 28 housing one or more wires 30. The elongate body 18 may also include one or more lumens for housing one or more pull wires and/or other steering elements (not shown). The treatment device 12 may be a focal catheter or may have any other configuration to which the mapping device 14 could be coupled. It will be understood that the one or more wires 30 and/or steering elements may be embedded within the elongate body 18 or located in a lumen shared with another device component instead of being located in a dedicated wire and/or steering element lumen.

Figure 8:
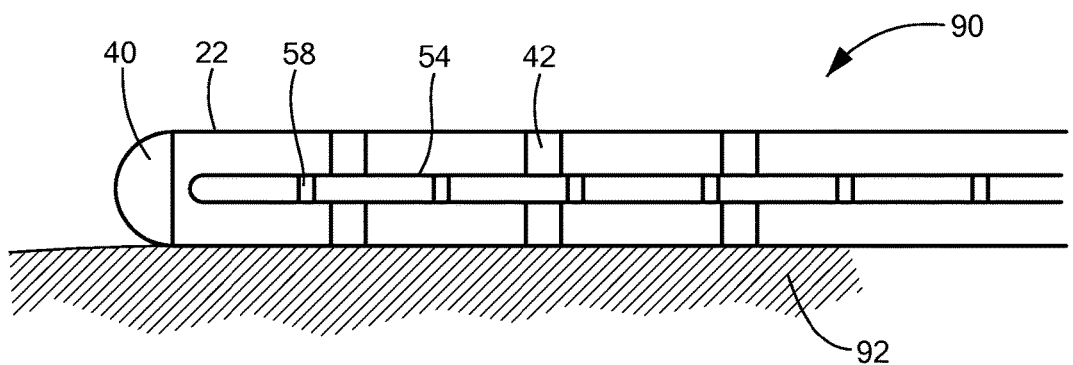
FIG. 8 shows a distal portion of a multi-function medical device, including a treatment device and a mapping device, in an at least substantially linear configuration and creating a linear ablation lesion.

The treatment device 12 may be configured to deliver various energy modalities (such as RF energy, electroporation energy, ultrasound energy, microwave energy, laser energy, or the like) and/or to cryogenically treat tissue. For example, the treatment device 12 may be a focal catheter that has a distal portion 22 with at least a portion of which being transitionable between an at least substantially linear configuration (for example, as shown in FIGS. 8 and 9) to create linear and/or focal lesions and an at least substantially circular configuration (for example, as shown in FIG. 10) to create wide-area and/or at least substantially circular lesions.

Figure 9:
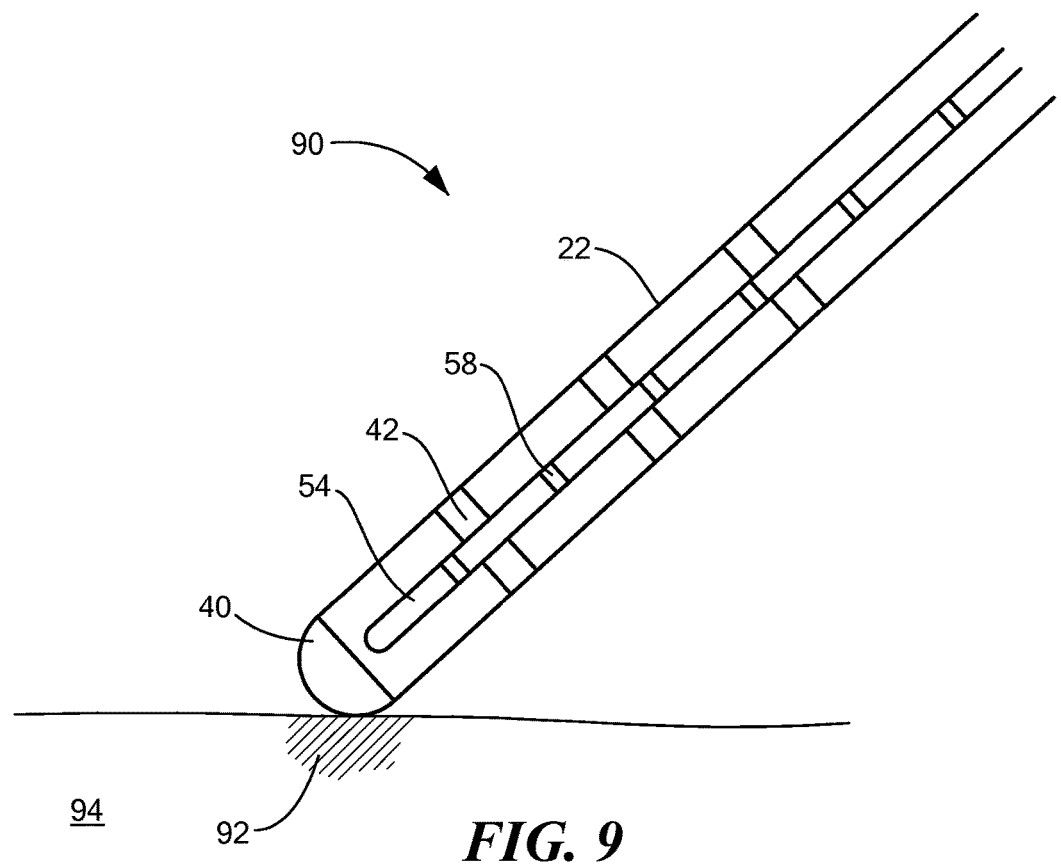
FIG. 9 shows a distal portion of a multi-function medical device, including a treatment device and a mapping device, in an at least substantially linear configuration and creating a focal ablation lesion.
Figure 10:
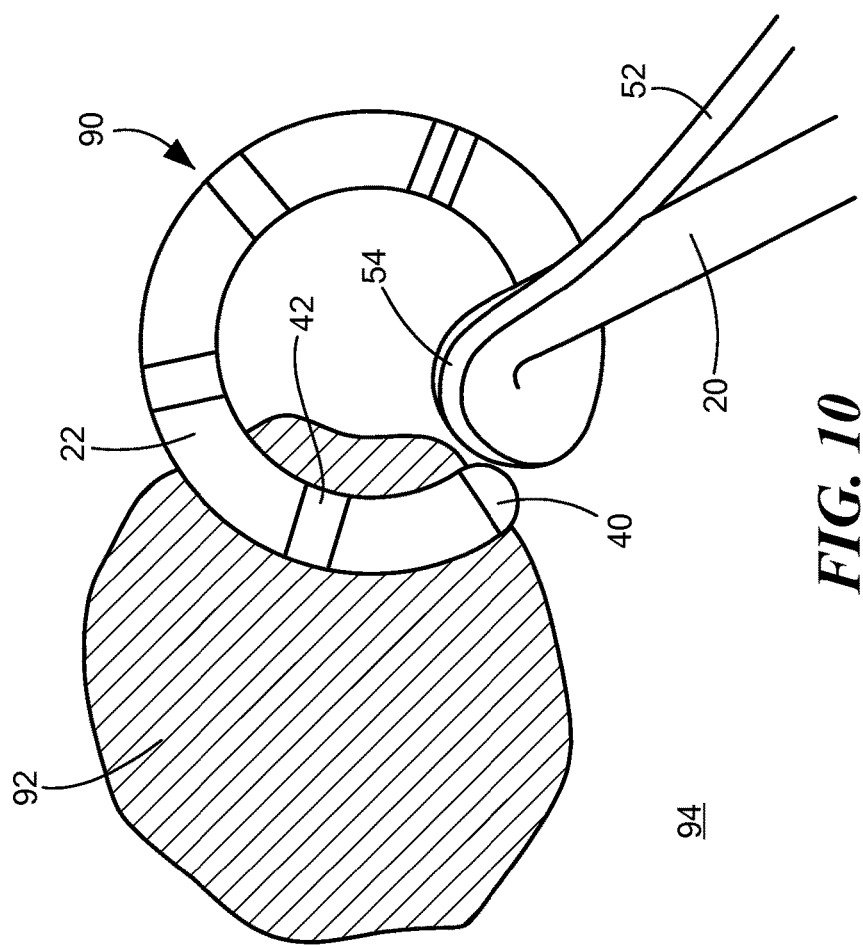
FIG. 10 shows a distal portion of a multi-function medical device, including a treatment device and a mapping device, in an at least substantially circular configuration and having created a wide-area, at least substantially circular ablation lesion.

Although the treatment device 12 is shown in FIG. 9 as creating a focal lesion when the distal portion 22 of the device 12 is in an at least substantially linear configuration, it will be understood that the device 12 may be used to produce focal lesions in other configurations as well. Further, the phrase "at least substantially liner" may refer to a configuration in which the distal portion 22 of the elongate body 20 has a longitudinal axis 34 and no bend or deflection that is greater than approximately 10°±5° from the longitudinal axis 34. Similarly, the phrase "at least substantially circular" may refer to a configuration in which the distal portion 22 of the elongate body 20 has at least one bend or deflection from the longitudinal axis 34 greater than approximately 10°±5° and defines an at least substantially circular shape (that is, a curvature of approximately 365°±45°) that lies in a plane that is at least substantially orthogonal to the longitudinal axis 34. During some procedures, the at least substantially circular shape may not lie in a plane that is at least substantially orthogonal to the longitudinal axis 34; however, the at least substantially circular shape may lie in a plane that intersects the longitudinal axis 34 and creates a wide-area and/or at least substantially circular ablation pattern when placed in contact with tissue.

Figure 5:
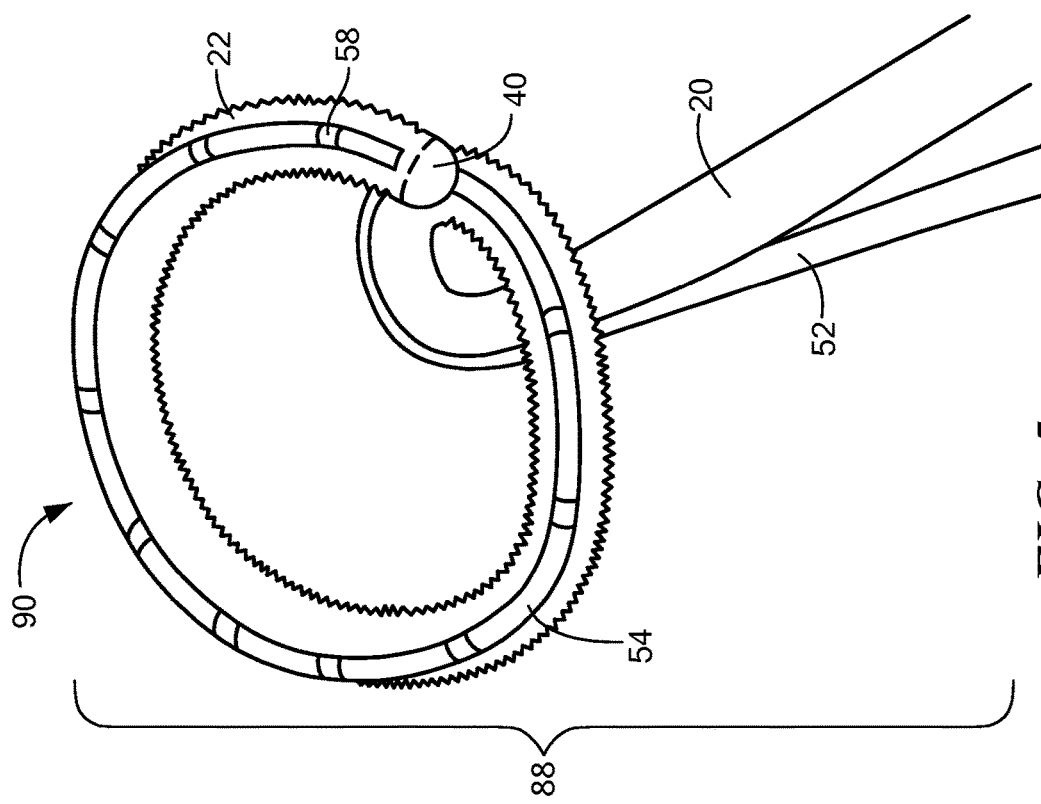
FIG. 5 shows a fourth embodiment of a distal portion of a treatment device and a distal portion of a mapping device, the distal portions of the treatment and mapping devices being coupled together to create a multi-function medical device.
Figure 4:
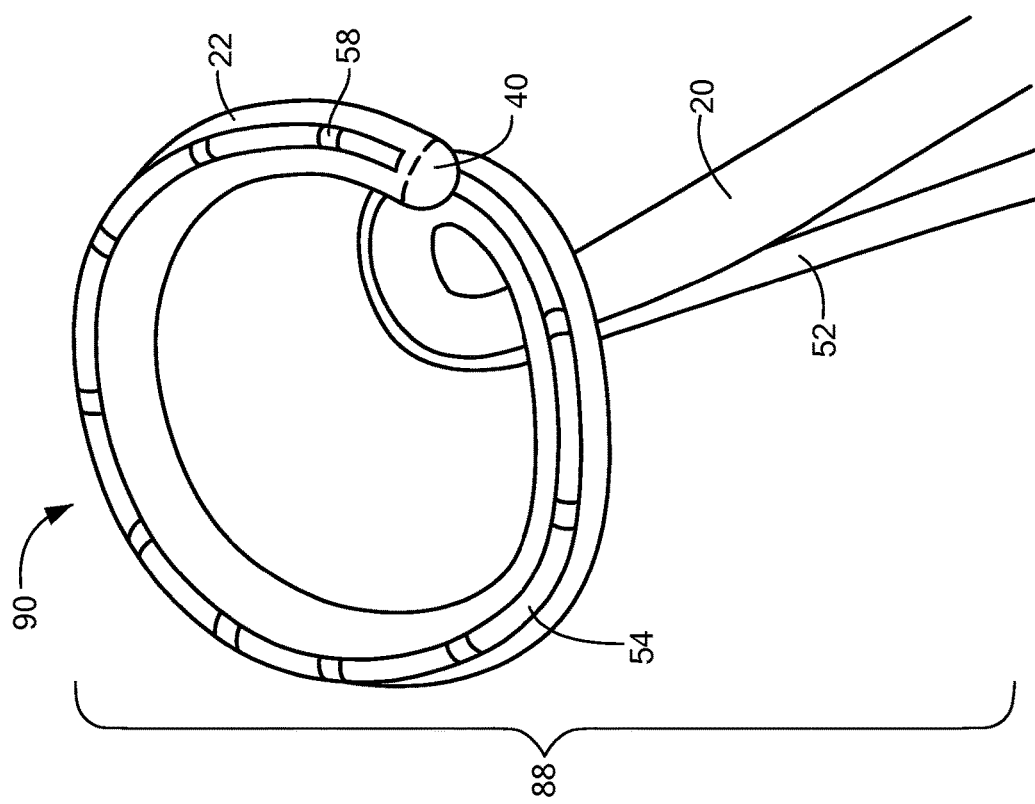
FIG. 4 shows a third embodiment of a distal portion of a treatment device and a distal portion of a mapping device, the distal portions of the treatment and mapping devices being coupled together to create a multi-function medical device.
Figure 7:
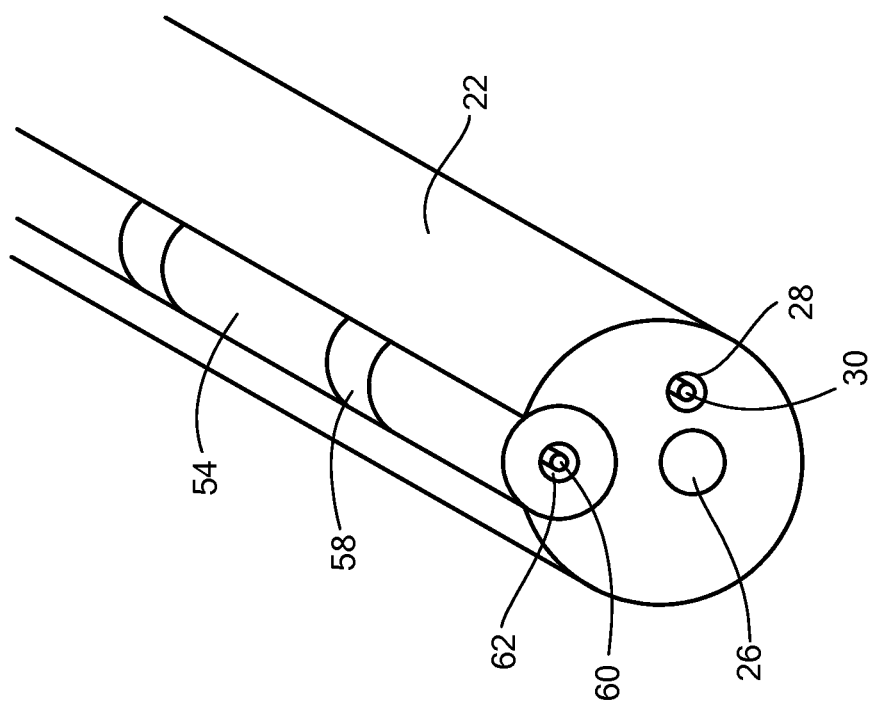
FIG. 7 shows a close-up, partially cross-sectional view of the distal portion of the treatment device as shown in FIG. 3 with a mapping device attached thereto.

The distal portion 20 of the treatment device 12 may include one or more electrodes for the exchange of energy between the treatment device 12 and an area of target tissue. The electrodes may be composed of a thermally transmissive material, such as metal. As a non-limiting example, the device 12 may include a distal tip electrode 40 and one or more other electrodes 42 disposed along the length of the distal portion 22 of the treatment device 12. For example, the figures show a treatment device 12 having a distal tip electrode 40 and a plurality of band electrodes 42 on the elongate body 18. However, it will be understood that the electrodes 42 may be of any size and configuration that allows the device to deliver treatment or ablation energy and/or to remove heat from tissue during a cryotreatment or cryoablation procedure. If the device 12 is configured to deliver RF or other energy, the electrodes 40, 42 may be in electrical communication with one or more wires 30 which are, in turn, in electrical communication with the control unit 16. Additionally or alternatively, if the device 12 is configured for cryotreatment (that is, the removal of heat from the target tissue), the electrodes 40, 42 may simply be thermally transmissive regions that are in thermal communication with the fluid injection lumen 26 within the elongate body 18. However, like the electrodes, the thermally transmissive regions may be composed of metal, although other thermally transmissive materials may additionally or alternatively be used. Still further, in some embodiments, the distal portion 22 of the treatment device 12 may not include any electrodes (for example, as shown in FIGS. 11-14) or discrete thermally transmissive areas, or may only include a distal tip electrode 40 (for example, as shown in FIGS. 4 and 5). In that case, the entire distal portion 22 or at least a part of the distal portion may be thermally transmissive such that when refrigerant is delivered to the distal portion 22, the entire distal portion is cooled.

The mapping device 14 may generally include an elongate body 50 having a proximal portion 52 and a distal portion 54. The proximal portion 52 of the elongate body 50 may be coupled to and in mechanical communication with a handle 56 having one or more steering actuators (not shown). The mapping device 14 may also include one or more mapping electrodes 58 that are capable of sensing electrograms from tissue (for example, cardiac tissue). The electrodes 58 may also be configured to deliver pacing energy to the tissue. The electrodes 58 may be in electrical communication with one or more wires 60 that are, in turn, in electrical communication with the control unit 16. The elongate body 50 may also have one or more wire lumens 62 for housing the one or more wires 60, or the wires 60 may be embedded in the elongate body 50 or located within a shared lumen. If the mapping device 14 is used to cryomap tissue, the elongate body 50 may include a fluid delivery lumen (not shown) that is in fluid communication with a refrigerant source for the delivery of refrigerant to the thermally transmissive areas 58. Additionally, the elongate body 50 may include one or more lumens (not shown), similar to those discussed above regarding the treatment device 12, for housing one or more other device components and/or steering mechanisms, such as pull wires.

Like the treatment device 12, the mapping device 14 may be transitionable between an at least substantially linear configuration (for example, as shown in FIGS. 8 and 9) and an at least substantially circular configuration (for example, as shown in FIG. 10). During a treatment procedure, the distal portion 22 of the treatment device 12 and the distal portion 54 of the mapping device 14 may be in the same configuration, as discussed in more detail below.

The control unit 16 may generally include all of the system components, other than the treatment device 12 and the mapping device 14, that are used to control, activate, navigate, and transmit and/or receive data and energy to and/or from the devices 12, 14. For example, the control unit 16 may include one or more umbilicals, one or more energy sources 66 in electrical communication with the treatment 12 and/or mapping 14 devices (such as a radiofrequency energy generator for delivering radio frequency energy and/or AC/DC electroporation energy to the electrodes 40, 42 of the treatment device and/or for delivering mapping energy to the electrodes 58 of the mapping device 14), a fluid reservoir 68 in fluid communication with the treatment device 12 to cool the thermally conductive areas 40, 42 (such as in an embodiment wherein the treatment device 12 is configured for cryotreatment), a source of contrast fluid (not shown), and one or more computers 70 having one or more displays 72, one or more processors 74, and one or more user input devices 76.

The control unit 16 may receive mapping data from the mapping device 14. For example, the one or more processors 74 may be programmed to execute one or more algorithms for the processing and interpretation of mapping data, and for communicating results to the user. As a non-limiting example, the one or more processors may use the received mapping data to locate an arrhythmogenic focus or rotor and to communicate the location to the user, such as by displaying mapping data (and/or text, colors, or graphics representing such data) on the one or more displays 72.

Figure 6:
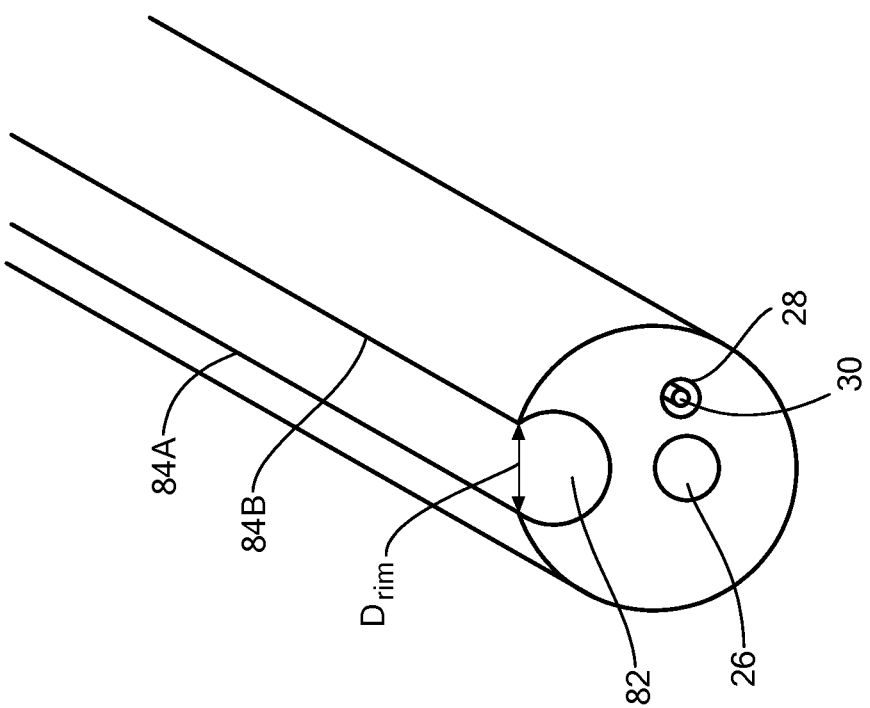
FIG. 6 shows a close-up, partially cross-sectional view of a distal portion of a treatment device without a mapping device.

Referring now to FIGS. 2-7, a distal portion of a treatment device and a distal portion of a mapping device are shown, the distal portions of the treatment and mapping devices being coupled together to create a multi-function medical device. The distal portion 22 of the elongate body 18 of the treatment device 12 may define or include a longitudinal groove 66 sized to accommodate and retain the distal portion 54 of the mapping device 14. That is, the distal portion 22 of the treatment device 12 may include a groove 82 having an inner diameter that is only slightly larger than an outer diameter of the distal portion 54 of the mapping device 14. Further, the groove may define a first longitudinal rim 84A and a second longitudinal rim 84B that are separated by a distance $D_{rim}$ that is slightly smaller than the outer diameter of the mapping device 14. In this manner, the distal portion 54 of the mapping device 14 may be coupled to the distal portion 22 of the treatment device 12 by inserting the distal portion 54 of the mapping device 14 into the groove 82 in the distal portion 22 of the treatment device 12. In other words, the distal portion 54 of the mapping device 14 may be "snapped into" the groove 82 in the distal portion 22 of the treatment device 12 (for example, as shown in FIG. 6). The distal portion 22 of the treatment device 12 may have a diameter that is greater than the diameter of the distal portion 54 of the mapping device 14, and the distal portion 54 of the mapping device 14 may protrude slightly from the groove 82 (for example, as shown in FIG. 6). The distal end of the groove 82 may terminate a distance proximal to the distal tip of the treatment device 12. For example, the distal end of the groove 82 may terminate proximal to the distal tip electrode 40. Further, although one or more electrodes 42 of the treatment device 12 may be referred to as band electrodes and/or may have other configurations, the electrodes 42 may not traverse the groove 82. The proximal portions 20, 52 of the treatment device 12 and the mapping device 14 may not be coupled together, and may, for example, be passed through a guide sheath or other delivery device and/or be located outside the patient's body in a side-by-side relationship.

Although the treatment device 12 and the mapping device 14 may be independently steerable and/or transitionable between an at least substantially linear configuration and an at least substantially circular configuration, the distal portion 22 of the treatment device 12 may be transitionable whereas the distal portion 54 of the mapping device 14 may not. In such a configuration, steering and/or deflection of the distal portion 22 of the treatment device 12 may cause the distal portion 54 of the mapping device 14 to assume the same shape as the distal portion 22 of the treatment device 12 when coupled together. The opposite may also be true, wherein the distal portion 54 of the mapping device 14 may be transitionable whereas the distal portion 22 of the treatment element 12 may not. In such a configuration, steering and/or deflection of the distal portion 54 of the mapping device 14 may cause the distal portion 22 of the treatment device 12 to assume the same shape as the distal portion 54 of the mapping device 14 when coupled together. When the treatment 12 and mapping 14 devices are coupled together, the resulting unit may be referred to as a multi-function device 88. Although both the treatment 12 and mapping 14 devices are shown in FIG. 1 has being attached to handles 24, 56, only one handle may be used for navigation, shaping, and/or activation of the multi-function device 88.

Figure 3:
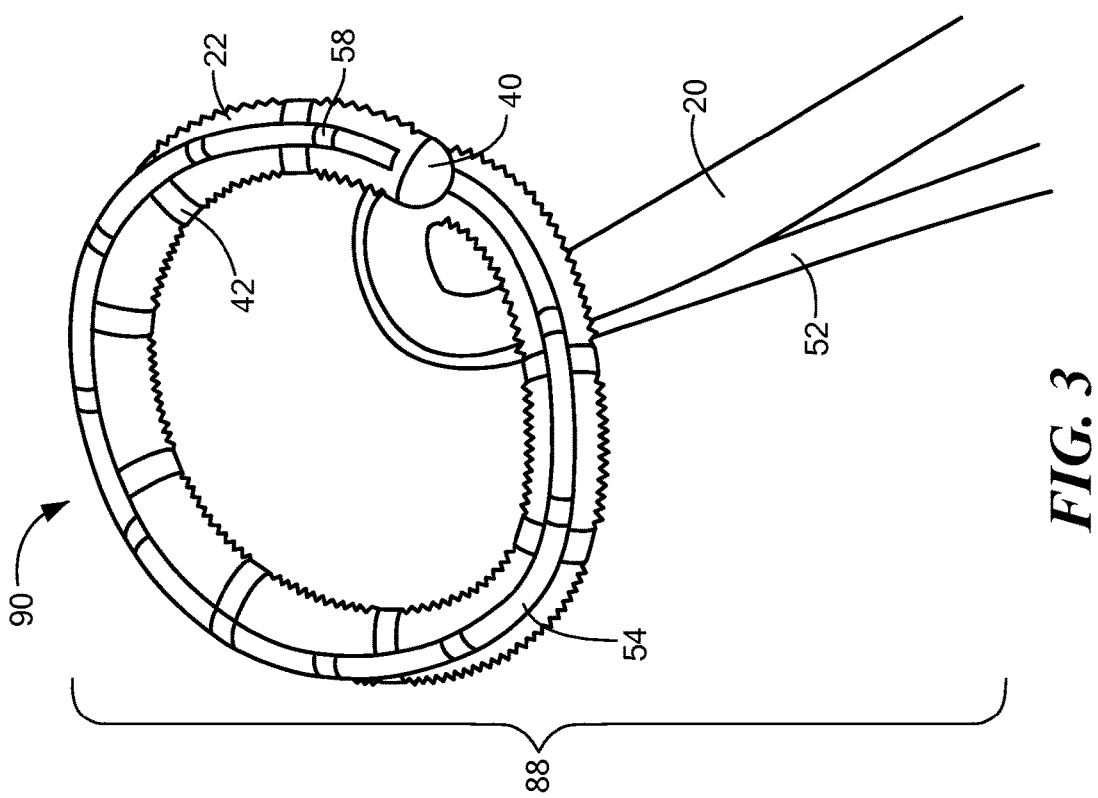
FIG. 3 shows a second embodiment of a distal portion of a treatment device and a distal portion of a mapping device, the distal portions of the treatment and mapping devices being coupled together to create a multi-function medical device.
Figure 2:
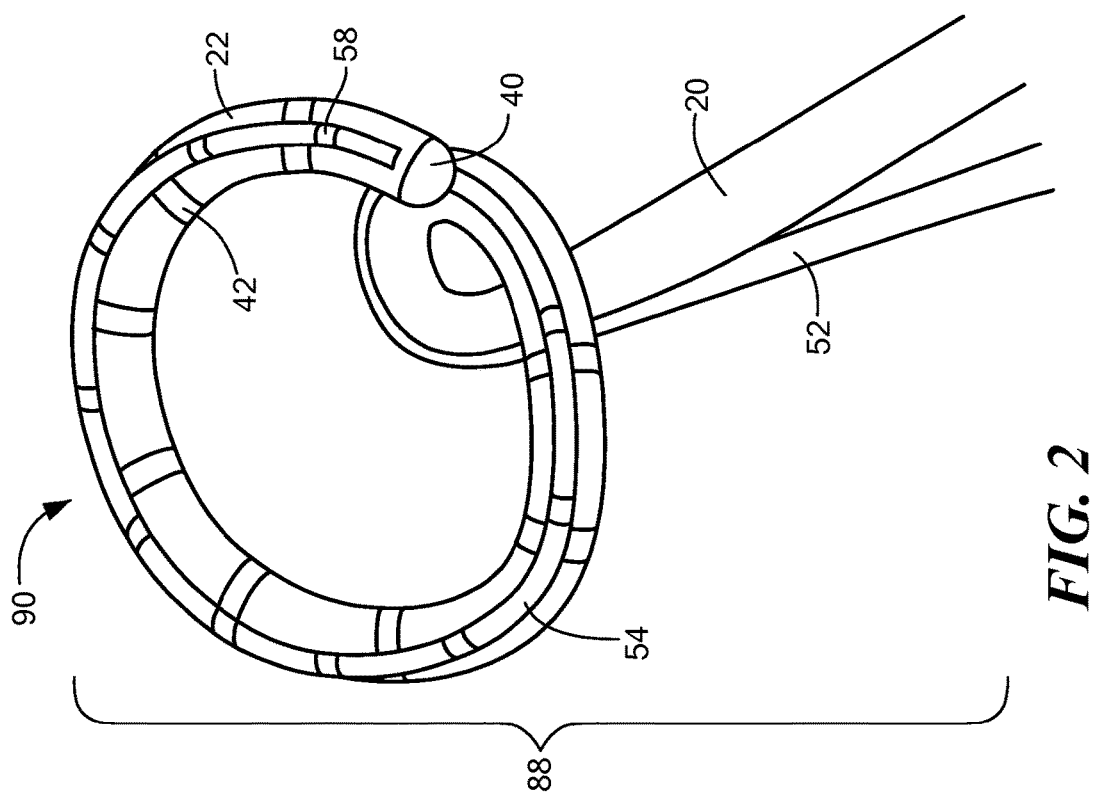
FIG. 2 shows a first embodiment of a distal portion of a treatment device and a distal portion of a mapping device, the distal portions of the treatment and mapping devices being coupled together to create a multi-function medical device.

The embodiments of the multi-function device 88 shown in FIGS. 2 and 3 may be substantially the same, except for the texture of the elongate body 18 of the treatment device 12. For example, at least the distal portion 22 of the elongate body 18 may be smooth or untextured as shown in FIG. 2, or it may be wrinkled or segmented to increase flexibility and avoid unwanted folds in the elongate body 18. As a non-limiting example, the distal portion 22 of the elongate body 18 is shown in FIG. 3 with a wrinkled texture. In either the embodiment shown in FIG. 2 or the embodiment shown in FIG. 3, at least the distal portion 22 of the elongate body 18 may be composed of a flexible biocompatible material, including but not limited to polymer, a polymer-PEBAX® combination, polyvinylchloride (PVC), polyurethane, silicone, plastic, or the like. In the embodiment shown in FIG. 3, at least the distal portion 22 of the elongate body 22 may additionally or alternatively be composed of metal. The proximal portion 20 of the treatment device elongate body 18 may be composed of the same material or a different material as that from which the distal portion 22 is composed.

Further, the embodiments of FIGS. 2 and 3 may be substantially the same as the embodiments shown in FIGS. 4 and 5, except that the embodiments shown in FIGS. 4 and 5 include only a distal tip electrode 40. The embodiment shown in FIG. 4 has a smooth texture, similar to the embodiment shown in FIG. 2, whereas the embodiment shown in FIG. 5 has a texture similar to the embodiment shown in FIG. 3. In the embodiments of FIGS. 4 and 5, the entire distal portion 22, or at least a portion of the distal portion 22, of the treatment device 12 may be thermally conductive without necessitating one or more electrodes coupled to, affixed to, or otherwise on the distal portion 22. As a non-limiting example, the distal portion 22 of the treatment device 12 may be a flexible (for example, segmented) metal body that is capable of assuming a variety of configurations, as shown and described herein. Alternatively, the distal portion 22 may be composed of an unsegmented, flexible, and thermally transmissive material.

Referring now to FIGS. 8-10, the distal portion of the multi-function catheter is shown in a variety of configurations. FIG. 8 shows the distal portion 90 of the multi-function device 88 (that is, the distal portions 22, 54 of the treatment device 12 and the mapping device 14, respectively) in an at least substantially linear configuration and creating a linear lesion 92 in an area of target tissue 94. The distal tip electrode 40 and the band electrodes 42 may be used to create the linear lesion, or the band electrodes 42 only may be used. If RF energy is delivered from the electrodes 42, the RF energy may be delivered in unipolar only mode, bipolar only mode, a combination of unipolar and bipolar modes, and/or a phased delivery. Linear lesions may be used, for example, to treat tissue on the roof or walls of the heart. FIG. 9 shows the distal portion 90 of the multi-function device 88 in an at least substantially linear configuration and creating a focal lesion 92 with the distal tip electrode 40. Although the distal portion 90 is shown as being in an at least substantially linear configuration, the distal portion 90 may be in any configuration that allows contact between the distal tip electrode 40 and tissue 94 for the creation of a focal lesion. FIG. 10 shows the distal portion 90 of the multi-function device 88 in an at least substantially circular configuration and having created a wide-area and/or at least substantially circular lesion 92. Similarly to the energy delivery discussed regarding FIG. 8, the electrodes 40 and/or 42 may deliver RF energy in a variety of modes. Wide-area and/or at least substantially circular lesions may be used to treat, for example, areas such as pulmonary vein ostia. The lesions shown in FIGS. 8-10 may also be created by delivering refrigerant from the fluid reservoir 68 to the distal portion 54 of the mapping device 14 (and therefore to the distal portion 90 of the multi-function device 88). Additionally or alternatively, other energy modalities may be used to energize the electrodes 40, 42 and create a variety of lesion shapes and sizes. Although a linear, focal, and at least substantially circular lesions 92 are shown, it will be understood that this is an exemplary representation of the variety of lesions that can be formed using the multi-function catheter 88. Although the lesions 92 are shown as being formed with electrodes 40, 42 in FIGS. 8-10, cryoablation may additionally or alternatively be used to ablate or treat tissue, such as with a device as shown and described in FIGS. 4, 5, and 11-14.

Figure 11:
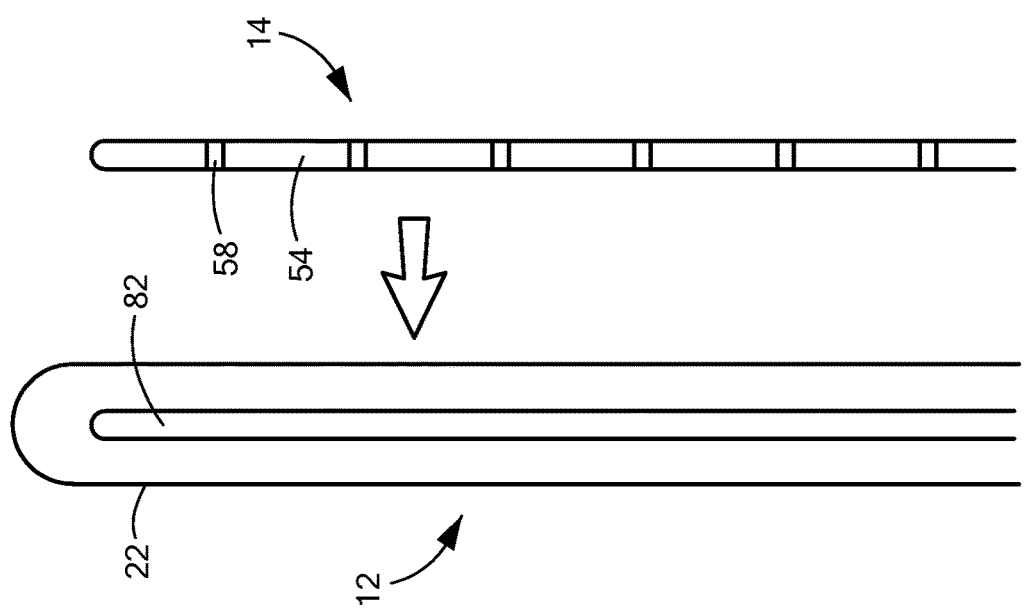
FIGS. 11-14 show an exemplary method of use of a multi-function device.
Figure 12:
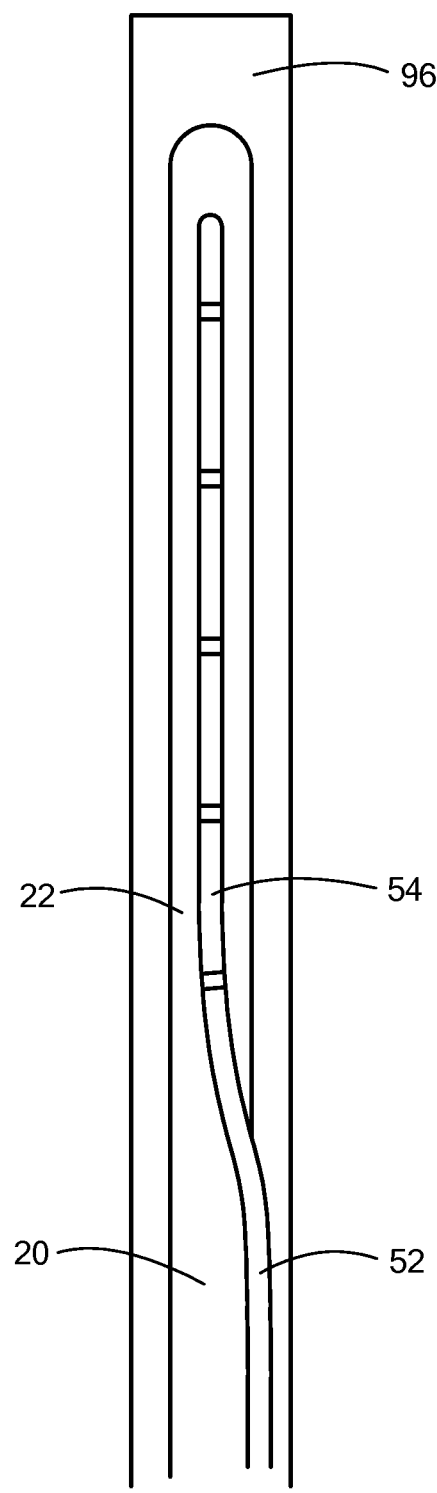

Referring now to FIGS. 11-14, an exemplary method of use of a multi-function device is shown. The distal portion 22 of the treatment device 12 may be coupled to the distal portion 54 of the mapping device 14, such as by being snapped into the groove 82 of the distal portion 22 of the treatment device (for example, as shown in FIG. 11), before the treatment 12 and mapping 14 devices, as the combined multi-function device 88, are inserted into the patient's vasculature. Further, the coupled distal portion 90 of the multi-function device 88 may be passed through a sheath or delivery device 96, whereas the proximal portions 20, 52 of the treatment 12 and mapping 14 devices, respectively, may be passed through the sheath 96 in a side-by-side relationship (for example, as shown in FIG. 12).

Figure 13:
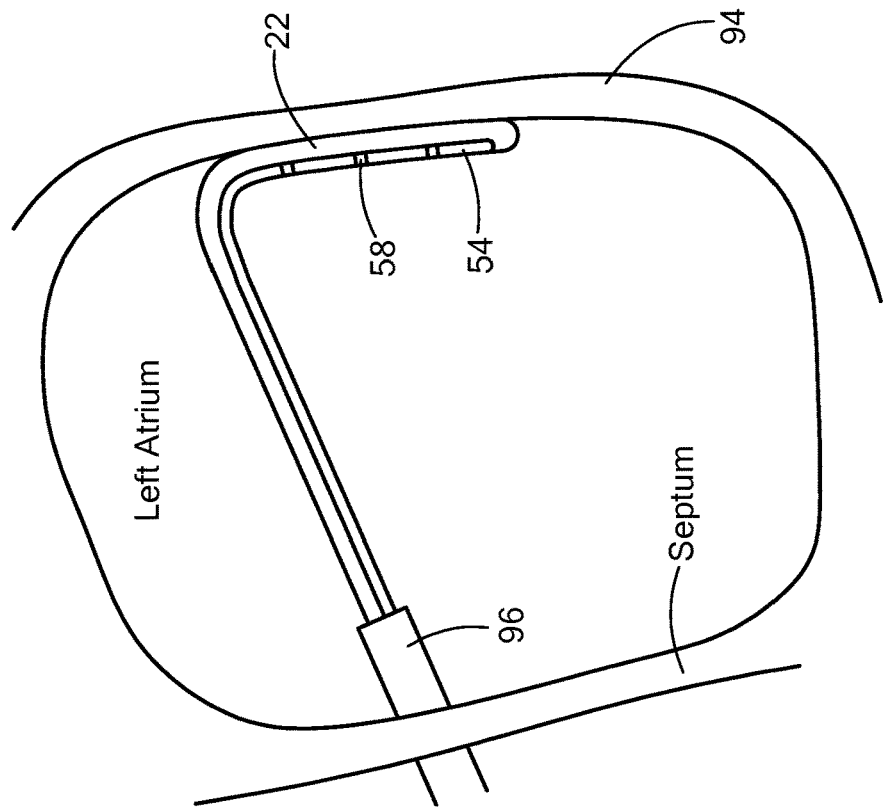

Once within the patient and proximate a tissue area, the distal portion 90 of the multi-function device 88 may be manipulated into any of a variety of configurations, such as those shown and described in FIGS. 8-10, and the mapping electrodes 58 may be placed in contact with tissue and used to record, for example, cardiac electrograms (for example, as shown in FIG. 13, wherein the multi-function device 88 is shown recording electrograms from a portion of the left atrial wall of a stylized depiction of a heart). It will be understood that the mapping electrodes 58 may be configured for or used to collect a variety of mapping data, and are not just limited to recording electrograms. The distal portion 90 of the multi-function device 88 may be moved around within the heart to collect data from a plurality of locations, until one or more arrhythmogenic foci (referred to as target treatment sites) are found. For example, the mapping electrodes 58 may be used to identify and locate one or more CFAEs, GPs, rotors, or the like.

Figure 14:
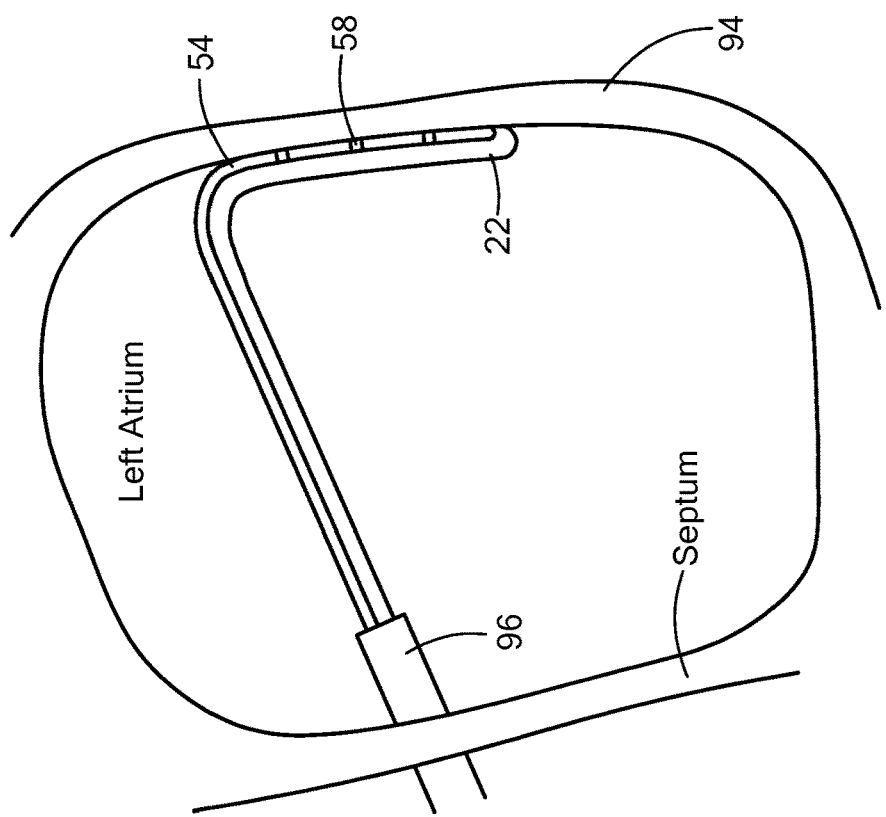

Once a target treatment site is identified, the distal portion 90 of the multi-function device 88 may be manipulated, or maintained in the same configuration as used for mapping, and the one or more electrodes 40 and/or 42, depending on the desired lesion type, may be placed in contact with the target treatment site (for example, as shown in FIG. 14, wherein the multi-function device 88 is shown recording electrograms from a portion of the left atrial wall). For example, when the distal portion 90 is in an at least substantially linear configuration, the distal portion 90 may be rotated slightly so the treatment electrodes 40 and/or 42 are in contact with tissue instead of the mapping electrodes 58. Ablation or treatment energy may be delivered to the one or more electrodes 40 and/or 42 to ablate or treat the target treatment site. Additionally or alternatively, refrigerant may be delivered to the thermally transmissive areas 40 and/or 42. Additionally or alternatively, refrigerant may be delivered to the distal portion 22 of the treatment device 12, the distal portion 22 not including any electrodes (as shown in FIG. 14) or just a distal tip electrode 40. In either case, the distal portion 22 may function like an ablation element, and the device may be rotated or positioned such that the thermally transmissive distal portion 22 is in contact with the tissue to create a cryoablation lesion. If the distal portion 22 includes a distal tip electrode 40, the distal tip electrode 40 may be used in addition to the distal portion 22 to create one or more lesions. The mapping device 14 does not need to be uncoupled from the treatment device 12 prior to delivering energy and/or refrigerant to the one or more electrodes 40 and/or 42 and/or delivering refrigerant to a thermally transmissive distal portion 22.

The multi-function catheter 88 shown and described herein may provide a device that has ablation/treatment and mapping functionality without increasing the size of the device and increasing the cost and complexity of the device's fabrication.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical system for treating and mapping tissue, the system comprising:
   a first elongate body including a first proximal portion and a first distal portion, the first distal portion including a longitudinal groove and at least one thermally transmissive region;
   a second elongate body including a second proximal portion and a second distal portion, the second distal portion including a plurality of mapping electrodes and being received and retained within the longitudinal groove of the first distal portion such that at least a portion of each of the mapping electrodes is received within the longitudinal groove; and
   a control unit in communication with the first elongate body and the second elongate bodies, the control unit receiving mapping data from the plurality of mapping electrodes and delivering at least one of treatment energy and refrigerant to the at least one thermally transmissive region to ablate the tissue when the system is in use,
   the coupled first distal portion and the second distal portion together being transitionable between an at least substantially linear first configuration and an at least substantially circular second configuration.

2. The medical system of claim 1, wherein the first elongate body defines a distal tip and an outer lateral surface, the at least one thermally transmissive region being a plurality of electrodes, the plurality of electrodes including a distal tip electrode and a plurality of electrodes on the outer lateral surface of the first elongate body.

3. The medical device of claim 2, wherein the plurality of electrodes on the outer lateral surface of the first elongate body do not traverse the longitudinal groove.

4. The medical system of claim 1, wherein the first distal portion and the second distal portion are coupled to each other when the first elongate body and the second elongate body are within a patient's body and the first proximal portion and the second proximal portion are uncoupled from each other when the first elongate body and the second elongate body are within the patient's body.

5. The medical system of claim 1, wherein the first distal portion has a wrinkled texture.

6. The medical system of claim 1, wherein the at least one thermally transmissive region includes a plurality of electrodes and the control unit includes at least one of an electroporation energy source and a radiofrequency energy source, each of the at least one of the electroporation energy source and the radiofrequency energy source being in electrical communication with the plurality of electrodes.

7. The medical system of claim 1, wherein the first elongate body defines a fluid delivery lumen and the control unit includes a refrigerant source, the fluid delivery lumen being in fluid communication with the refrigerant source and in thermal communication with the at least one thermally transmissive region.

8. A method of mapping and treating cardiac tissue, comprising:

positioning at least a portion of a medical device within a patient's heart, the medical device including:
  an ablation catheter having a proximal portion and a distal portion having a plurality of treatment electrodes and defining a longitudinal groove; and
  a mapping catheter having a proximal portion and a distal portion having a plurality of mapping electrodes, the distal portion of the mapping catheter being within and retained by the longitudinal groove of the ablation catheter such that at least a portion of each of the plurality of mapping electrodes is received within the longitudinal groove and at least a portion of each of the plurality of mapping electrodes is not received within the longitudinal groove;
positioning the medical device such that the at least a portion of each of the plurality of mapping electrodes that is not received within the longitudinal groove is in contact with an area of tissue of the patient's heart;
recording mapping data with the plurality of mapping electrodes while the mapping catheter is within and retained by the longitudinal groove of the ablation catheter;
positioning the medical device such that the plurality of treatment electrodes are in contact with an area of tissue of the patient's heart; and
delivering ablation energy from the plurality of treatment electrodes while the mapping catheter is within and retained by the longitudinal groove of the ablation catheter.

9. The method of claim 8, wherein the distal portion of the treatment catheter and the distal portion of the mapping catheter together define a distal portion of the medical device when the distal portion of the mapping catheter is within and retained by the longitudinal groove of the ablation catheter, the distal portion of the medical device being transitionable between an at least substantially linear first configuration and an at least substantially circular second configuration.

10. The medical device of claim 8, wherein the proximal portion of the treatment catheter and the proximal portion of the mapping catheter are not coupled to each other when the at least a portion of the medical device is within the patient's body.

* * * * *